United States Patent
Cai et al.

(10) Patent No.: US 10,702,280 B2
(45) Date of Patent: Jul. 7, 2020

(54) ENDOSCOPIC REPOSABLE SURGICAL CLIP APPLIER

(71) Applicant: Covidien LP, Mansfield, MA (US)

(72) Inventors: Longsheng Cai, Shanghai (CN); Shunhong Xu, Shanghai (CN); Lin Chen, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 198 days.

(21) Appl. No.: 15/773,181

(22) PCT Filed: Nov. 10, 2015

(86) PCT No.: PCT/CN2015/094195
§ 371 (c)(1),
(2) Date: May 3, 2018

(87) PCT Pub. No.: WO2017/079895
PCT Pub. Date: May 18, 2017

(65) Prior Publication Data
US 2018/0317927 A1    Nov. 8, 2018

(51) Int. Cl.
*A61B 17/128* (2006.01)
*A61B 17/00* (2006.01)
*A61B 34/35* (2016.01)

(52) U.S. Cl.
CPC .......... *A61B 17/1285* (2013.01); *A61B 34/35* (2016.02); *A61B 2017/00407* (2013.01); *A61B 2017/00464* (2013.01); *A61B 2017/00477* (2013.01)

(58) Field of Classification Search
CPC . A61B 17/068; A61B 17/128; A61B 17/1285; A61B 34/35; A61B 2017/00407; A61B 2017/00477; A61B 2017/00464
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

International Search Report corresponding to Int'l Patent Appln. PCT/US2018/050316 dated Dec. 31, 2018.

(Continued)

*Primary Examiner* — Eric J Rosen
*Assistant Examiner* — Mohammed S Adam

(57) ABSTRACT

Endoscopic reposable surgical clip appliers including a reusable handle assembly and at least one reusable shaft assembly.

8 Claims, 13 Drawing Sheets

(56) References Cited

U.S. PATENT DOCUMENTS

| | | |
|---|---|---|
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,156,609 A * | 10/1992 | Nakao ............... A61B 17/0682 227/179.1 |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |

(56) References Cited

U.S. PATENT DOCUMENTS

| | | |
|---|---|---|
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,601,601 A * | 2/1997 | Tal .................. A61B 17/29 606/174 |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,002 A * | 1/1999 | Desai .................. A61B 8/0841 606/139 |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |

(56) References Cited

U.S. PATENT DOCUMENTS

| | | |
|---|---|---|
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |

(56) References Cited

U.S. PATENT DOCUMENTS

| | | |
|---|---|---|
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huiterna |
| 8,839,954 B2 | 9/2014 | Disch |

(56) References Cited

U.S. PATENT DOCUMENTS

| | | |
|---|---|---|
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,883,866 B2 | 2/2018 | Roundy et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2004/0232201 A1* | 11/2004 | Wenchell .......... A61B 17/068 227/176.1 |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0234478 A1* | 10/2005 | Wixey ................ A61B 17/12 606/142 |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |

(56) References Cited

U.S. PATENT DOCUMENTS

| | | |
|---|---|---|
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0068990 A1* | 3/2007 | Shelton, IV ..... A61B 17/07207 227/175.1 |
| 2007/0083218 A1 | 4/2007 | Morris |
| 2007/0093790 A1 | 4/2007 | Downey et al. |
| 2007/0093856 A1* | 4/2007 | Whitfield ........... A61B 17/1285 606/142 |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0250113 A1* | 10/2007 | Hegeman ......... A61B 17/00234 606/207 |
| 2007/0260257 A1* | 11/2007 | Phan ................ A61B 17/1617 606/84 |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0057103 A1* | 3/2010 | Sorrentino ............. A61B 17/10 606/143 |
| 2010/0072258 A1* | 3/2010 | Farascioni ....... A61B 17/07207 227/180.1 |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0095481 A1* | 4/2012 | Bouduban .......... A61B 17/0469 606/148 |
| 2012/0116388 A1* | 5/2012 | Houser ................. A61N 7/00 606/41 |
| 2012/0116389 A1* | 5/2012 | Houser ................ A61B 34/25 606/41 |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172910 A1 | 7/2013 | Malkowski |
| 2013/0175320 A1 | 7/2013 | Mandakolathur Vasudevan et al. |
| 2013/0193188 A1* | 8/2013 | Shelton, IV ........... A61B 34/76 227/175.2 |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0106434 A1* | 4/2016 | Blake, III .......... A61B 17/1285 606/143 |
| 2016/0113655 A1* | 4/2016 | Holsten .............. A61B 17/1285 606/143 |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0290583 A1* | 10/2017 | Reed ................ A61B 17/07207 |
| 2017/0290587 A1 | 10/2017 | Schober et al. |
| 2018/0021041 A1 | 1/2018 | Zhang et al. |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0069915 A1* | 3/2019 | Mansfield .......... A61B 1/00085 |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |

(56) References Cited

U.S. PATENT DOCUMENTS

| | | | |
|---|---|---|---|
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | | |
|---|---|---|---|
| CN | 1939228 A | 4/2007 |
| CN | 103251441 A | 8/2013 |
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0514139 A3 | 3/1993 |
| EP | 0732078 A2 | 9/1996 |
| EP | 1769757 A1 | 4/2007 |
| EP | 2158856 A2 | 3/2010 |
| EP | 2815702 A1 | 12/2014 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2010051810 A | 3/2010 |
| JP | 2011186812 A | 9/2011 |
| JP | 2012505046 A | 3/2012 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2014172477 A2 | 10/2014 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Extended European Search Report issued in corresponding European Application No. 15908025.8 dated Jul. 2, 2019, 8 pages.
Japanese Office Action issued in corresponding Japanese Application No. 2018-521373 dated Aug. 20, 2019, 6 pages.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report for PCT/CN2015/094195 date of completion is Jul. 14, 2016 (5 pages).

* cited by examiner

ENDOSCOPIC REPOSABLE SURGICAL CLIP APPLIER

CROSS-REFERENCE TO RELATED APPLICATIONS

This application is a National Stage Application of PCT/CN2015/094195 under 35 USC § 371 (a), the disclosure of the above-identified application is hereby incorporated by reference in its entirety.

BACKGROUND

Technical Field

The technical field relates to surgical clip appliers. More particularly, the present disclosure relates to endoscopic surgical clip appliers having handle assemblies configured for use with various different endoscopic assemblies.

Description of Related Art

Endoscopic surgical staplers and surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often use a particular endoscopic surgical clip applier to apply a surgical clip to a blood vessel or another duct to prevent the flow of body fluids therethrough during the procedure.

Endoscopic surgical clip appliers having various sizes (e.g., diameters), that are configured to apply a variety of diverse surgical clips, are known in the art, and which are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

Endoscopic surgical clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic surgical clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable endoscopic surgical clip applier. The endoscopic surgical clip applier advances and forms multiple clips during a single insertion into the body cavity. This resterilizable endoscopic surgical clip applier is configured to receive and cooperate with an interchangeable clip magazine so as to advance and form multiple clips during a single entry into a body cavity.

During endoscopic or laparoscopic procedures it may be desirable and/or necessary to use different size surgical clips or different configured surgical clips depending on the underlying tissue or vessels to be ligated. In order to reduce overall costs of an endoscopic surgical clip applier, it is desirable for a single endoscopic surgical clip applier to be loadable with and capable of firing different size surgical clips as needed.

Accordingly, a need exists for endoscopic surgical clip appliers that include handle assemblies configured for use with various different endoscopic assemblies having different clips loaded therein and/or configured for performing various different surgical tasks.

SUMMARY

The present disclosure relates to reposable endoscopic surgical clip appliers.

Provided in accordance with aspects of the present disclosure is a handle assembly of a reposable surgical clip applier configured to releasably engage at least two different endoscopic clip-applying assemblies. The handle assembly includes a housing, a trigger pivotably connected to the housing and movable relative thereto between an un-actuated position and an actuated position, and a drive bar slidably supported within the housing and operably coupled to the trigger such that movement of the trigger from the un-actuated position towards the actuated position translates the drive bar distally through the housing. The drive bar includes a ratchet rack disposed thereon. The handle assembly further includes a pawl pin supported within the housing and extending transversely relative to a longitudinal axis of the housing, a ratchet pawl pivotably and slidably supported on the pawl pin, and a bypass assembly. The ratchet pawl is transversely slidable about the pawl pin between a use position, wherein the ratchet pawl is aligned relative to the ratchet rack to engage the ratchet rack upon distal translation of the drive bar, and a bypass position, wherein the ratchet pawl is offset relative to the ratchet rack to inhibit engagement therewith upon distal translation of the drive bar. The bypass assembly includes a plunger slidably disposed within the housing and operably coupled to the ratchet pawl. The plunger is movable between a first position and a second position for sliding the ratchet pawl between the use position and the bypass position.

The bypass assembly may further include a first cam component slidably engaged with the plunger and a second cam component slidably disposed on the ratchet pawl. In such aspects, movement of the plunger from the first position to the second position urges the first cam component into the second cam component to thereby urge the second cam component to slide the ratchet pawl from the use position to the bypass position. More specifically, the first and second cam components may be configured such that longitudinal translation of the plunger effects transverse sliding of the ratchet pawl.

A first biasing member may be positioned to bias the ratchet pawl towards the use position. Additionally or alternatively, a second biasing member may be positioned to bias the plunger towards the first position.

The plunger may include a manual button extending from the housing that is selectively depressible relative to the housing to move the plunger from the first position to the second position.

Provided in accordance with other aspects of the present disclosure is a reposable surgical clip applier including a handle assembly and an endoscopic clip-applying assembly. The handle assembly includes a receiver assembly configured to releasably engage the endoscopic clip-applying assembly therein and including an outer collar and an inner tubular member. The handle assembly further includes a rotation knob disposed about the receiver assembly that is slidable relative to the inner tubular member and engaged to the outer collar such that sliding of the rotation knob relative to the inner tubular member between a proximal position and a distal position slides the outer collar relative to the inner tubular member between a proximal locked position and a distal unlocked position. The endoscopic clip-applying assembly is insertable into the inner tubular member. With the endoscopic clip-applying assembly inserted into the inner tubular member, the rotation knob is slidable from the distal position to the proximal position to thereby slide the outer collar from the distal unlocked position to the proximal locked position to lock the endoscopic clip-applying assembly within the inner tubular member.

One or more ball bearings may be configured for insertion partially through a respective aperture defined within the inner tubular member. Each ball bearing is configured for receipt within a corresponding aperture defined within the endoscopic clip-applying assembly to lock the endoscopic clip-applying assembly within the inner tubular member. In the proximal locked position of the outer collar, the outer collar urges the ball bearing(s) inwardly partially through the respective aperture of the inner tubular member and into engagement within the corresponding aperture defined within the endoscopic clip-applying assembly to lock the endoscopic clip-applying assembly within the inner tubular member.

The inner tubular member may define a proximal aperture and a distal aperture. In such aspects, the rotation knob may include a locking pin operably coupled thereto that is configured for engagement within the proximal aperture to lock the rotation knob in the proximal position and configured for engagement within the distal aperture to lock the rotation knob in the distal position.

In the absence of the endoscopic clip-applying assembly, the rotation knob may be locked in the distal position with the locking pin engaged within the distal aperture. Insertion of the endoscopic clip-applying assembly into the inner tubular member disengages the locking pin from the distal aperture to permit movement of the rotation knob to the proximal position.

A biasing member configured to bias the rotation knob towards the proximal position may be provided such that, upon disengagement of the locking pin from the distal aperture, the rotation knob is urged to the proximal position under the bias of the biasing member.

BRIEF DESCRIPTION OF THE DRAWINGS

Aspects and features of the presently-disclosed endoscopic surgical clip applier are described in detail with reference to the drawing figures wherein like reference numerals identify similar or identical structural elements and.

DETAILED DESCRIPTION OF EMBODIMENTS

Figure 1:
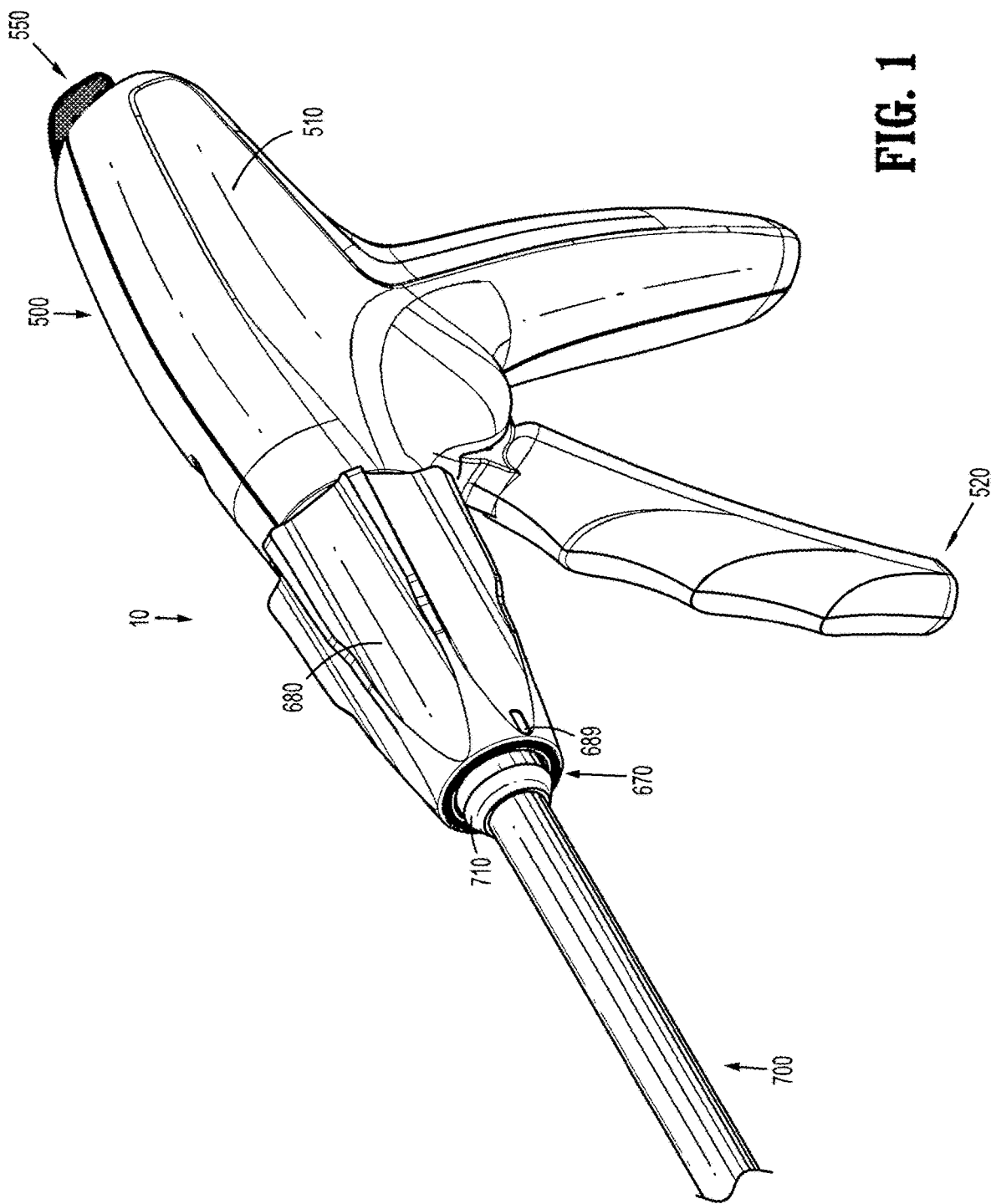
FIG. 1 is a perspective view of the proximal portion of an endoscopic surgical clip applier provided in accordance with the present disclosure including a handle assembly having an endoscopic assembly engaged therewith.
Figure 2:
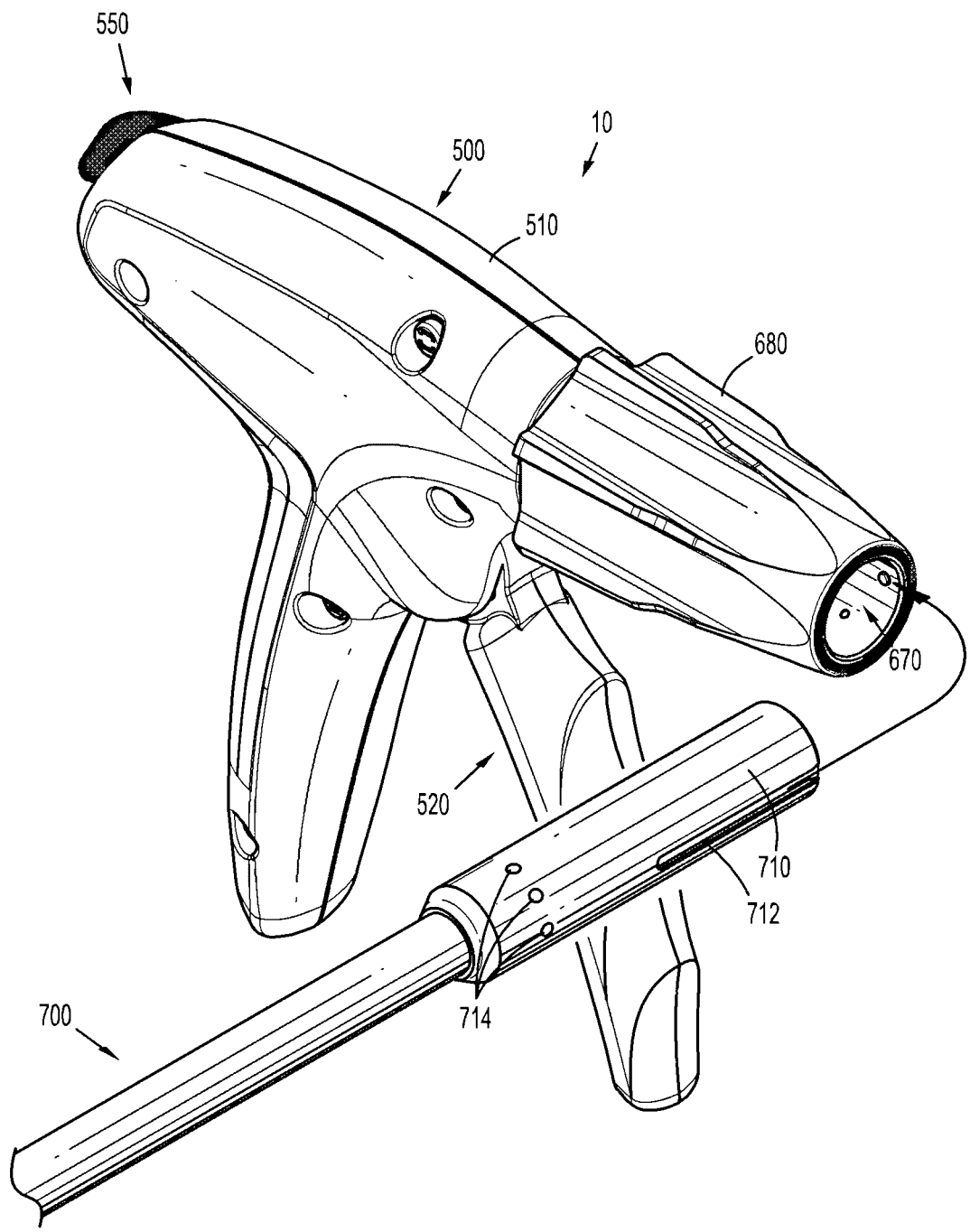
FIG. 2 is perspective view of the endoscopic surgical clip applier of FIG. 1 with the endoscopic assembly removed from the handle assembly.

Turning to FIGS. 1 and 2, an endoscopic surgical clip applier provided in accordance with the present disclosure is identified by reference numeral 10. Surgical clip applier 10 generally includes a handle assembly 500 and a plurality of endoscopic assemblies 700 selectively connectable to and extendable distally from handle assembly 100. Handle assembly 500 is advantageously configured to operate each of the plurality of endoscopic assemblies 700, upon connection thereto, and may be configured as a sterilizable, reusable component such that handle assembly 600 may be repeatedly used with different and/or additional endoscopic assemblies 700 during the course of one or more surgical procedures. The endoscopic assemblies 700 may be configured as single-use disposable components, limited-use disposable components, or reusable components, depending upon a particular purpose and/or the configuration of the particular endoscopic assembly 700. In either configuration, the need for multiple handle assemblies 500 is obviated and, instead, the surgeon need only select an appropriate endoscopic assembly 700 and connect that endoscopic assembly 700 to handle assembly 500 in preparation for use.

Handle assembly 500 is initially detailed, followed by a description of the use of handle assembly 500 in connection with a generic endoscopic assembly 700 that includes features common to any endoscopic assembly usable with handle assembly 500. Exemplary embodiments of particular endoscopic assemblies, e.g., endoscopic assembly 300 (FIG. 15) and endoscopic assembly 400 (FIG. 16), are thereafter detailed. Endoscopic assembly 300 (FIG. 15), for example, is configured for grasping and manipulating tissue, retrieving a surgical clip, and firing and forming the surgical clip about tissue. Endoscopic assembly 400 (FIG. 16), as another example, includes at least one surgical clip loaded therein and is configured to sequentially fire and form the at least one surgical clip about tissue. It is also envisioned that various other endoscopic assemblies for performing various different surgical tasks and/or having various different configurations may be provided for use with handle assembly 500.

Figure 3:
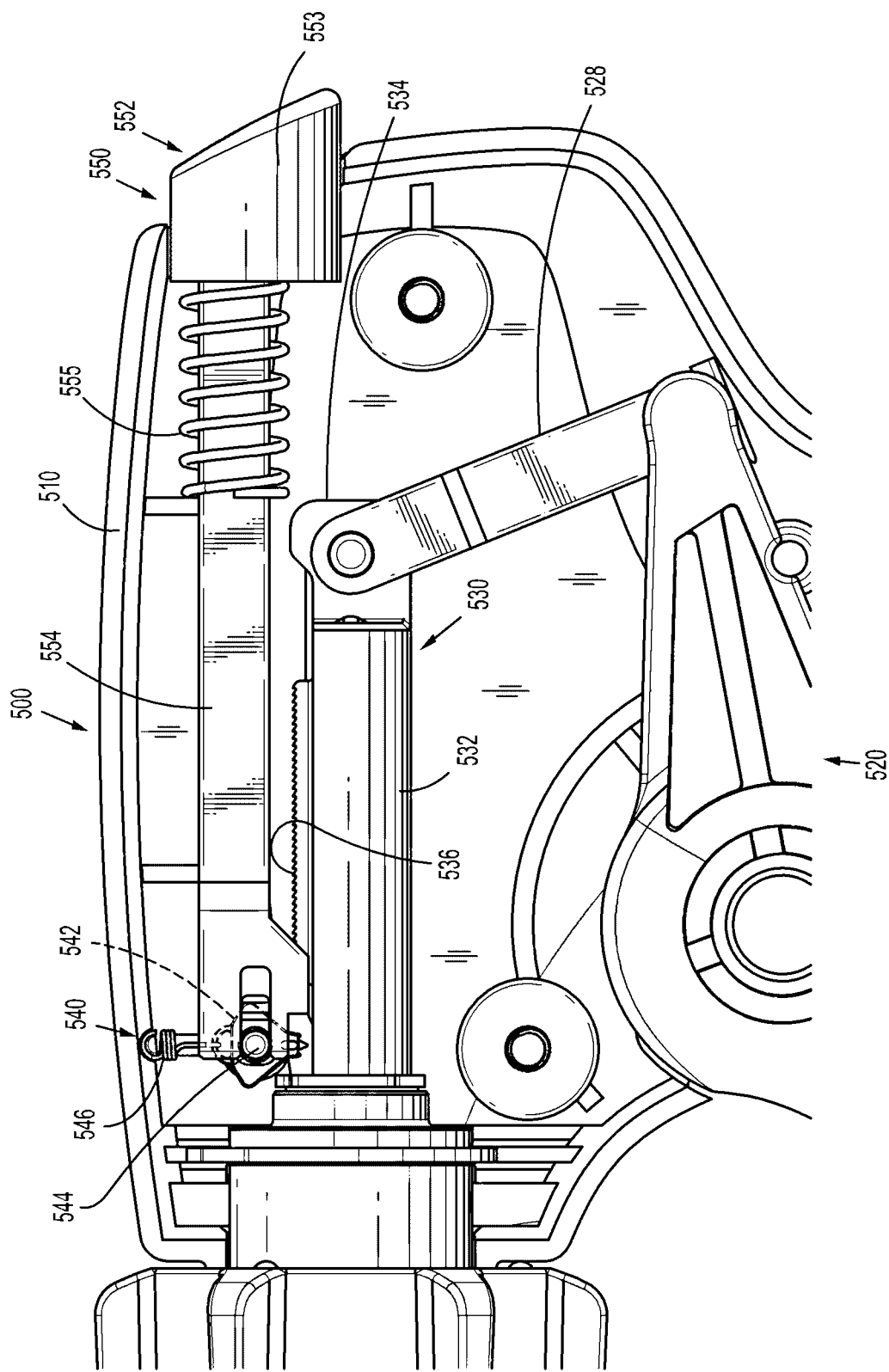
FIG. 3 is a side view of a portion of another reusable handle assembly provided in accordance with the present disclosure, with half of the housing removed to illustrate the internal components therein.

Referring to FIGS. 1-3, handle assembly 500 generally includes a housing 510, a trigger assembly 520 pivotably coupled to housing 510, a ratcheting drive assembly 530 operably coupled to trigger assembly 520, a bypass assembly 550 which is operably coupled to ratcheting drive assembly 530, a receiver assembly 670, and a rotation knob 680.

Referring to FIG. 3, ratcheting drive assembly 530 includes a drive bar 532 and a pawl assembly 540. Drive bar 532 includes a proximal extension 534 and a ratchet rack 536. Proximal extension 534 operably couples drive bar 532 to trigger assembly 520 via a linkage 528. As such, actuation of trigger assembly 520 translates drive bar 532 distally through housing 510 to fire the endoscopic assembly attached to handle assembly 500.

Pawl assembly 540 of ratcheting drive assembly 530 includes a ratchet pawl 542, a pawl pin 544, and a pawl biasing member 546. Ratchet pawl 542 is pivotably coupled to housing 510 by pawl pin 544 such that, in the use position (FIG. 6) thereof, ratchet pawl 542 is biased into operable position via pawl biasing member 546 so as to enable operable engagement of ratchet pawl 542 with ratchet rack 536 during advancement of drive bar 532 to enable ratcheting operation of ratcheting drive assembly 530. Ratchet pawl 542 is slidable transversely about pawl pin 544 from the use position (FIG. 6) to a bypass position (FIG. 7), as detailed below, to displace ratchet pawl 542 relative to ratchet rack 536, thereby disabling ratcheting operation of ratcheting drive assembly 530.

Figure 4:
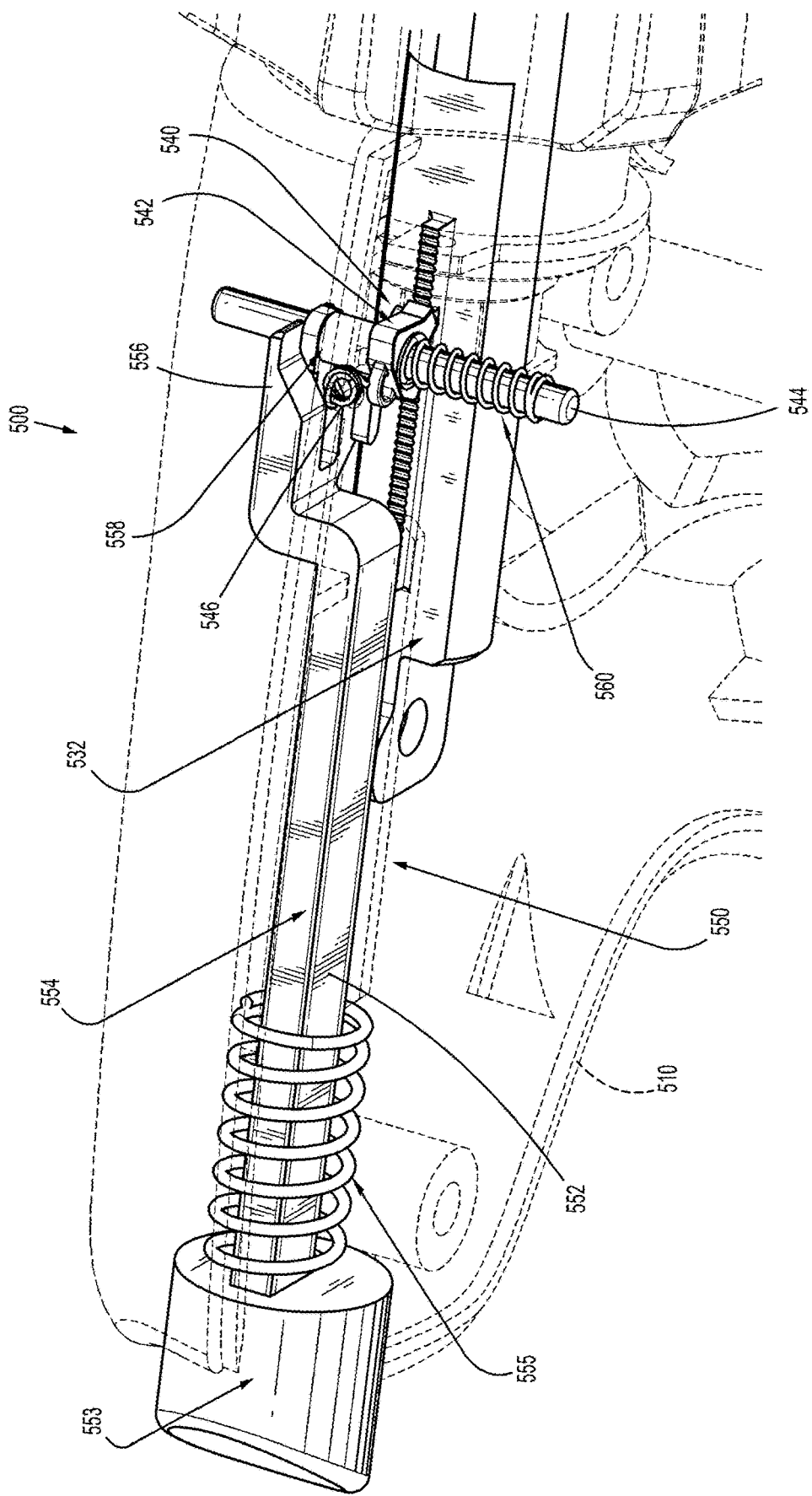
FIG. 4 is a top, perspective view of the portion of the reusable handle assembly of FIG. 3, with one half of the housing removed and the other half of the housing shown transparent to illustrate the internal components therein.
Figure 5:
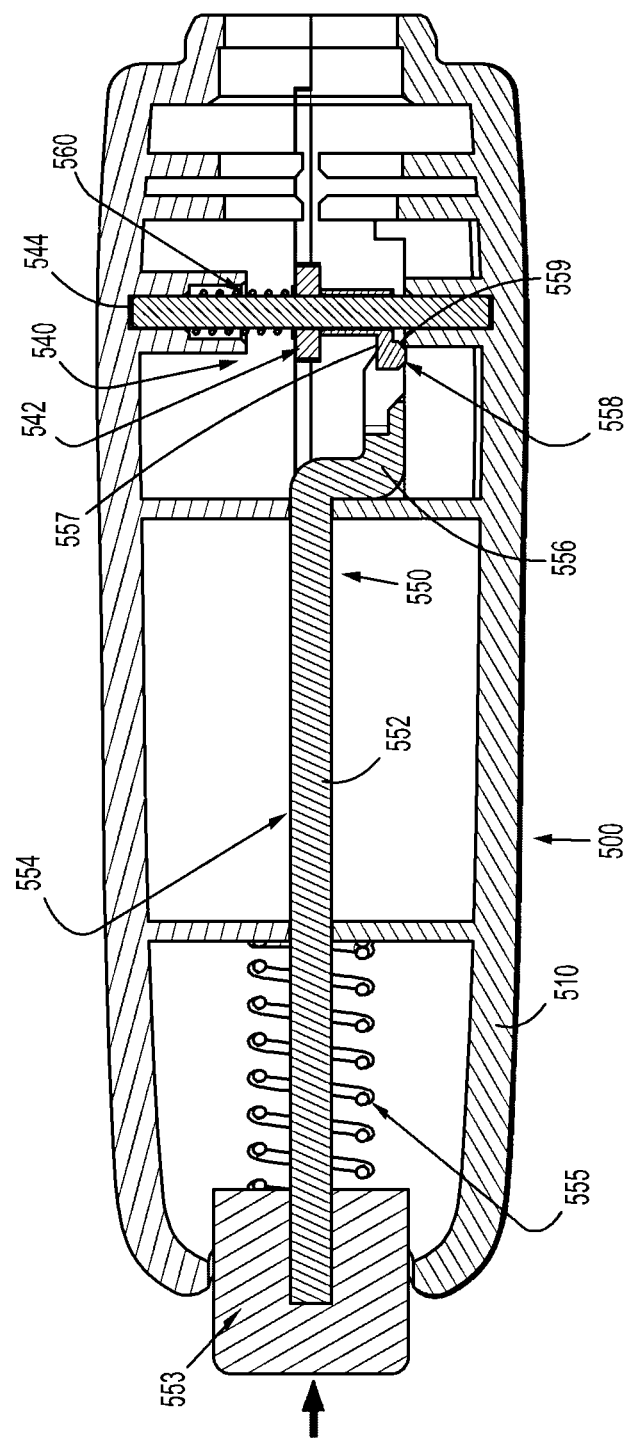
FIG. 5 is a top, longitudinal, cross-sectional view of the portion of the reusable handle assembly of FIG. 3.

With additional reference to FIGS. 4 and 5, bypass assembly 550 is operably coupled to pawl assembly 540 and includes a plunger 552, a first biasing member 555, a cam shaft 556, a cam sleeve 558, and a second biasing member 560. Plunger 552 includes a proximal button 553 and an elongated shaft 554 extending distally from proximal button 553. Proximal button 553 extends proximally from housing 510 so as to enable a user to selectively depress proximal button 553 inwardly into housing 510. Depression of proximal button 553 inwardly into housing 510 urges elongated shaft 554 distally through housing 510. First biasing member 555 is disposed about elongated shaft 554 and positioned so as to bias plunger 552 proximally towards a proximal position, while depression of proximal button 553 inwardly into housing urges plunger 552 from the proximal position to a distal position.

Cam shaft 556 is fixedly engaged, e.g., monolithically formed or otherwise fixed, with elongated shaft 554 of plunger 552 and extends distally therefrom. Cam shaft 556 defines a bifurcated distal end that receives a portion of pawl pin 544 therebetween. Each bifurcated portion of the distal end of cam shaft 556 defines a first angled cam surface 557. Cam sleeve 558 is disposed about pawl pin 544 between the bifurcated distal end of cam shaft 556 and ratchet pawl 542. Cam sleeve 558 defines a pair of second angled cam surfaces 559 disposed in abutting relation with first angled cam surfaces 557 of cam shaft 556. Second biasing member 560 is disposed about pawl pin 544 and positioned between ratchet pawl 542 and housing 510 (see FIGS. 4 and 5) so as to bias ratchet pawl 542 towards the use position (FIG. 6) thereof.

Figure 6:
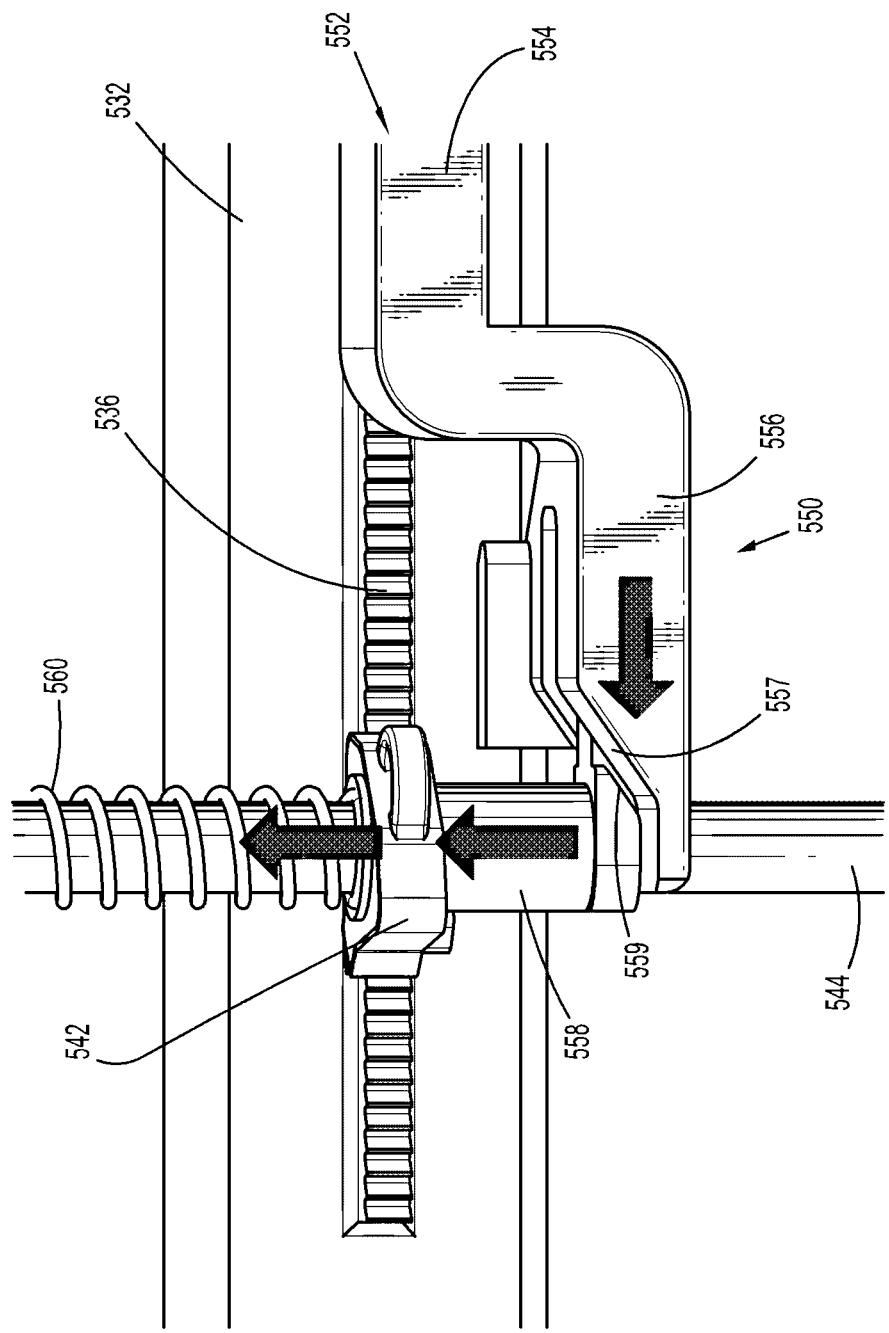
FIG. 6 is a top view of the ratcheting drive assembly and bypass assembly of the reusable handle assembly of FIG. 3, with the pawl disposed in an engaged position.
Figure 7:
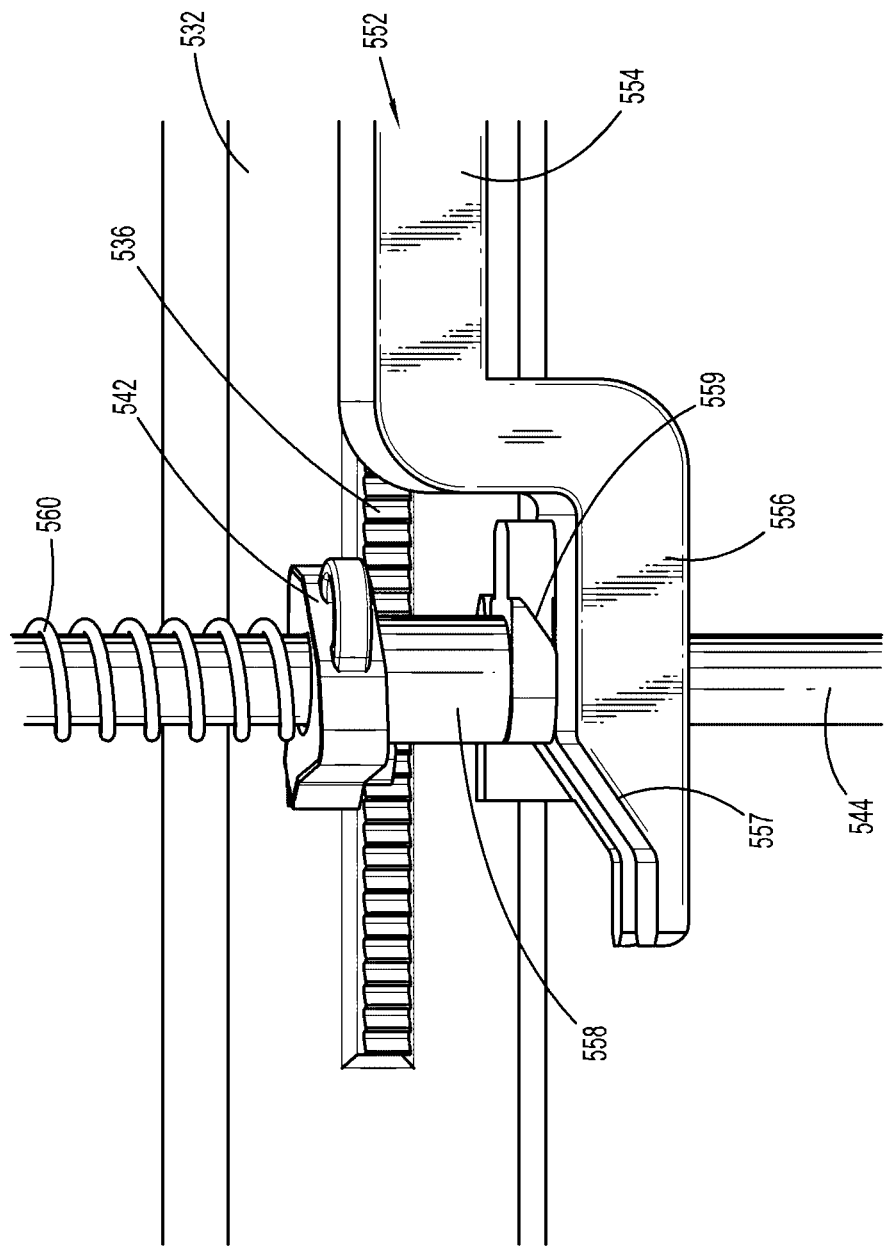
FIG. 7 is a top view of the ratcheting drive assembly and bypass assembly of the reusable handle assembly of FIG. 3, with the pawl disposed in a disengaged position.

Referring to FIGS. 6 and 7, in the proximal position of plunger 552, second biasing member 560 biases ratchet pawl 542 towards the use position (FIG. 6) thereof, wherein ratchet pawl 542 is positioned to enable operable engagement of ratchet pawl 542 with ratchet rack 536 during advancement of drive bar 533 to enable ratcheting operation of ratcheting drive assembly 530. When plunger 552 is depressed to the distal position thereof, plunger 552 is translated distally such that cam shaft 556 is likewise translated distally to urge first angled cam surfaces 557 of cam shaft 556 distally into second angled cam surfaces 559 of cam sleeve 558. Due to the angled configurations of first and second angled cam surfaces 557, 559, respectively, distal urging of cam shaft 556 into cam sleeve 558 urges cam sleeve 558 transversely along pawl pin 544 into contact with ratchet pawl 542 to thereby urge ratchet pawl 542 against the bias of second biasing member 560 from the use position (FIG. 6) to the bypass position (FIG. 7). In the bypass position, ratchet pawl 542 is offset from ratchet rack 536 to inhibit ratcheting during actuation.

Upon release of plunger 552, plunger 552 is returned to the proximal position under the bias of first biasing member 555 and ratchet pawl 542 is returned to the use position (FIG. 6) under the bias of second biasing member 560. However, it is also contemplated that bypass assembly 550 include a releasable locking mechanism (not shown) so as to enable releasable locking of plunger 552 in the distal position, thereby releasably locking ratchet pawl 542 in the bypass position (FIG. 7).

Figure 8:
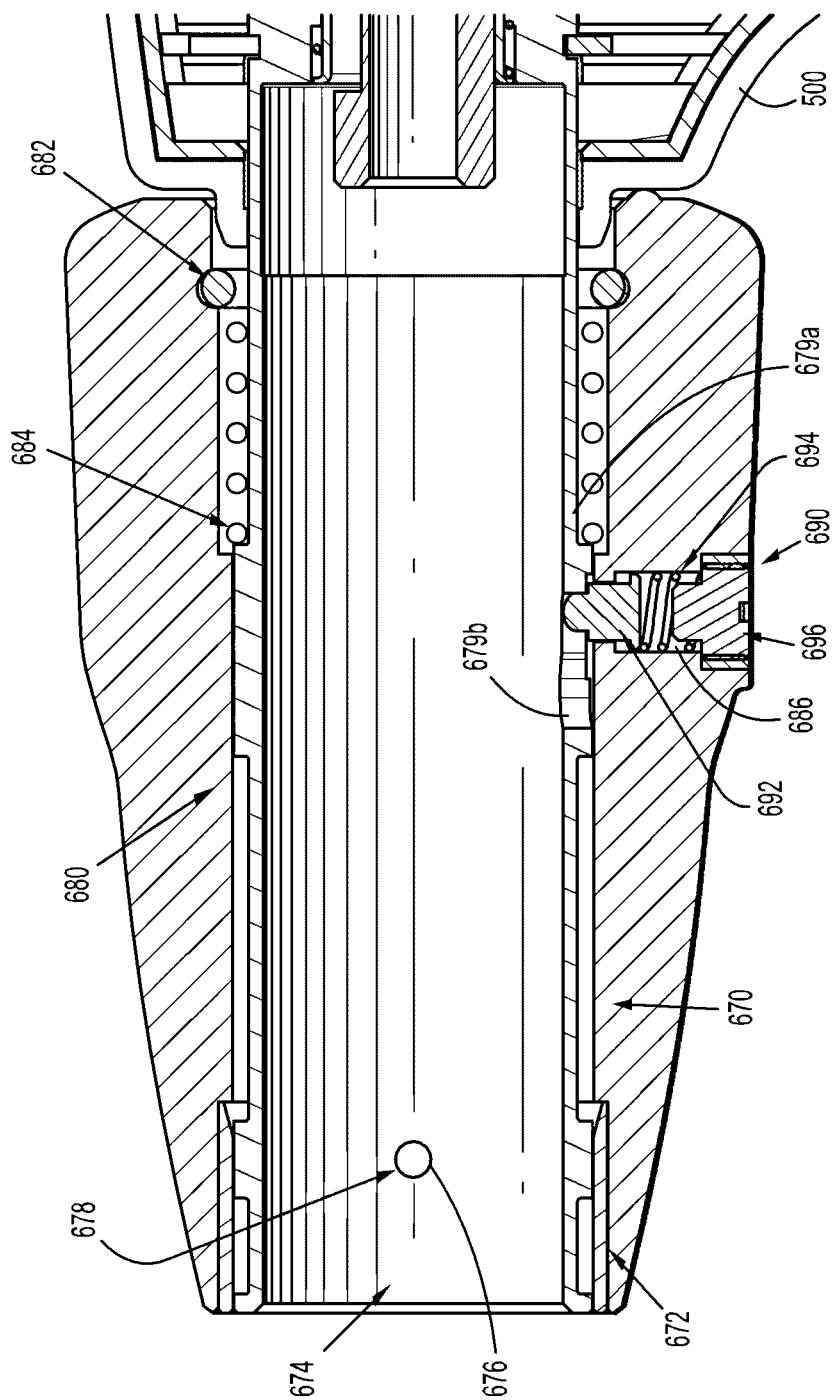
FIG. 8 is a side, longitudinal, cross-sectional view of the receiver assembly of the reusable handle assembly of FIG. 3.

Referring to FIGS. 1, 2, and 8, surgical clip applier 10 further includes a receiver assembly 670 extending from handle assembly 500 and configured to receive a proximal hub 710 of an endoscopic clip-applying assembly 700, for releasably engaging endoscopic clip-applying assembly 700 with handle assembly 500. Receiver assembly 670 includes an outer collar 672 and an inner tubular member 674. A rotation knob 680 is operably coupled to and disposed about receiver assembly 670, as detailed below. Inner tubular member 674 is fixed to handle assembly 500 and extends distally therefrom. Inner tubular member 674 defines an interior diameter slightly larger than an exterior diameter of proximal hub 710 of endoscopic clip-applying assembly 700 to enable slidable insertion of proximal hub 710 into inner tubular member 674 without significant play therebetween. Inner tubular member 674 further includes a plurality of apertures 676 defined therethrough and positioned circumferentially about inner tubular member 674. Apertures 676 are configured to permit portions, but not the entireties, of ball bearings 678 to extend therethrough into the interior thereof.

Inner tubular member 674 of receiver assembly 670 further defines proximal and distal apertures 679a, 679b, respectively, disposed adjacent one another and extending through inner tubular member 674 into the interior thereof. Although disposed adjacent one another, proximal and distal apertures 679a, 679b, respectively, are separated by a portion of inner tubular member 674 so as to inhibit direct communication therebetween. The function of proximal and distal apertures 679a, 679b, respectively, is detailed below.

Outer collar 672 of receiver assembly 670 is disposed about the distal end of inner tubular member 674 and engaged with rotation knob 680. Outer collar 672 is slidable with rotation knob 680 and relative to inner tubular member 674 between an un-locked distal position and a locked proximal position. In the locked proximal position, outer collar 672 urges ball bearings 678 inwardly such that portions of ball bearings 678 extend through apertures 676 of inner tubular member 674 into the interior of inner tubular member 674.

As noted above, rotation knob 680 is operably coupled to and disposed about receiver assembly 670. Rotation knob 680, more specifically, is slidably disposed about inner tubular member 674 of receiver assembly 670 and engages outer collar 762 of receiver assembly 670. A retaining ring 682 provides friction between rotation knob 680 and inner tubular member 674 to maintain rotation knob 680 in position in the absence of sufficient urging applied thereto. A biasing member 684 is positioned to bias rotation knob 680 proximally relative to inner tubular member 674, as detailed below. Rotation knob 680 is slidable about inner tubular member 674 between a proximal position, wherein rotation knob 680 abuts handle assembly 500 or is disposed in closer proximity thereto, and a distal position, wherein rotation knob 680 is spaced, or further spaced, from handle assembly 500. Since outer collar 672 is engaged with rotation knob 680, sliding of rotation knob 680 between the proximal position and the distal position slides outer collar 672 between the locked proximal position and the un-locked distal position.

A lock assembly 690 is operably disposed within a transverse aperture 686 defined through rotation knob 680. Lock assembly 690 includes a locking pin 692, a biasing member 694, and a set screw 696. Locking pin 692 is configured for engagement within proximal aperture 679a of inner tubular member 674 in the proximal position of rotation knob 680, and within distal aperture 679b of inner tubular member 674 in the distal position of rotation knob 680 to lock rotation knob 680 relative to inner tubular member 674 of receiver assembly 670, as detailed below. Set screw 696 retains biasing member 694 within transverse aperture 686 such that biasing member 694 biases locking pin 692 inwardly into the interior of rotation knob 680.

Figure 9:
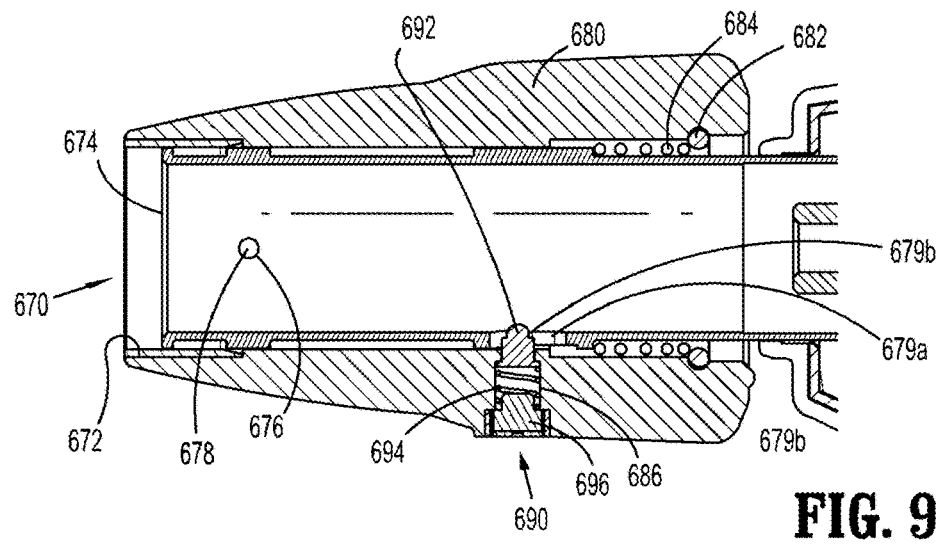
FIG. 9 is a side, longitudinal, cross-sectional view of the receiver assembly of the reusable handle assembly of FIG. 3, wherein the rotation knob is disposed in a distal position.

Referring to FIGS. 9-14, the use and operation of receiver assembly 670 and rotation knob 680 for releasably engaging an endoscopic clip-applying assembly 700 therein is detailed. Initially, as illustrated in FIG. 9, receiver assembly 670 is vacant, rotation knob 680 is disposed in the distal position, outer collar 672 is disposed in the unlocked distal position, and locking pin 692 is engaged within distal aperture 679b of inner tubular member 674 to lock rotation knob 680 and outer collar 672 relative to inner tubular member 674.

Figure 10A:
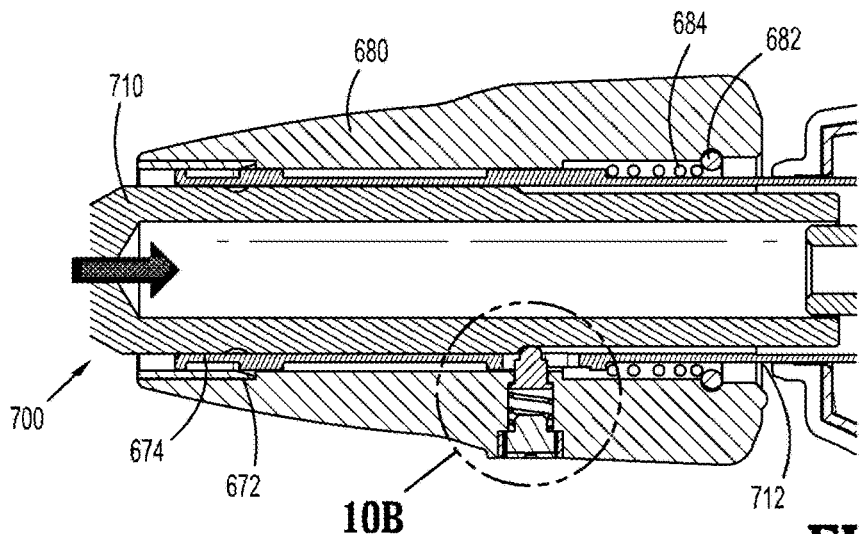
FIG. 10A is a side, longitudinal, cross-sectional view of the receiver assembly of the reusable handle assembly of FIG. 3, with the rotation knob is disposed in the distal position and an endoscopic assembly being inserted into engagement therewith.
Figure 10B:
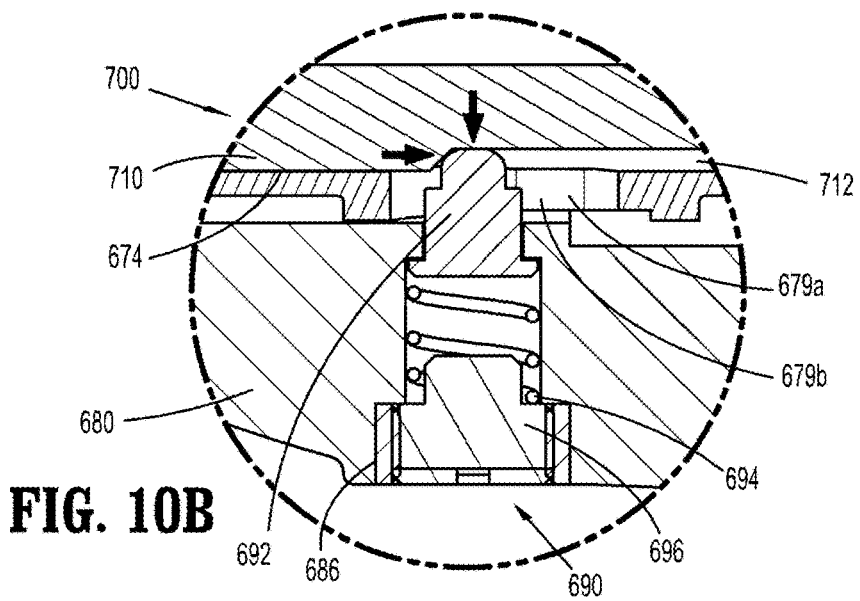
FIG. 10B is an enlarged side, longitudinal, cross-sectional view of the indicated area in FIG. 10A.

With reference to FIGS. 10A and 10B, in order to engage endoscopic clip-applying assembly 700 within receiver assembly 670, proximal hub 710 of endoscopic clip-applying assembly 700 is inserted into and slid proximally relative to inner tubular member 674. In order to insert proximal hub 710 of endoscopic clip-applying assembly 700 into inner tubular member 674 of receiver assembly 670, elongated channel 712 defined within the exterior of proximal hub 710 is aligned with locking pin 692, which, as noted above, at this point, extends through distal aperture 679b of inner tubular member 674 and into the interior of inner tubular member 674. Rotation knob 680 may include an alignment indicator 689 (FIG. 1) disposed on the exterior thereof to facilitate such alignment.

Upon initial proximal sliding of proximal hub 710 of endoscopic clip-applying assembly 700 into inner tubular member 674 of receiver assembly 670, locking pin 692 is translated through elongated channel 712 and remains engaged within distal aperture 679b, thereby maintaining rotation knob 680 locked relative to inner tubular member 674 in the distal position.

Figure 11:
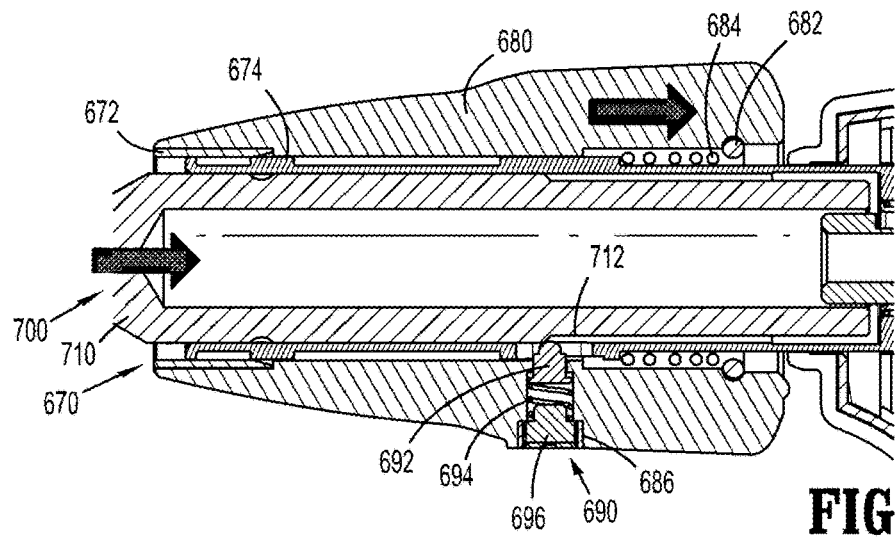
FIG. 11 is a side, longitudinal, cross-sectional view of the receiver assembly of the reusable handle assembly of FIG. 3, with the rotation knob disposed in a distal position and the endoscopic assembly disposed therein.

Referring additionally to FIG. 11, during insertion of proximal hub 710 of endoscopic clip-applying assembly 700 into inner tubular member 674 of receiver assembly 670, locking pin 692 eventually reaches the end of elongated channel 712 such that, upon further insertion of proximal hub 710 into inner tubular member 674 to a fully inserted position, the exterior surface of proximal hub 710 urges locking pin 692 outwardly, thereby disengaging locking pin 692 from distal aperture 679b, as shown in FIG. 11. In this fully inserted position, ball bearings 678 of inner tubular member 674 are aligned with apertures 714 of proximal hub 710 but are not yet engaged therewith. As detailed below, the subsequent movement of rotation knob 680 from the distal position to the proximal position to, in turn, move outer collar 672 from the unlocked distal position to the locked proximal position completes the engagement of proximal hub 710 within receiver assembly 670.

Figure 12A:
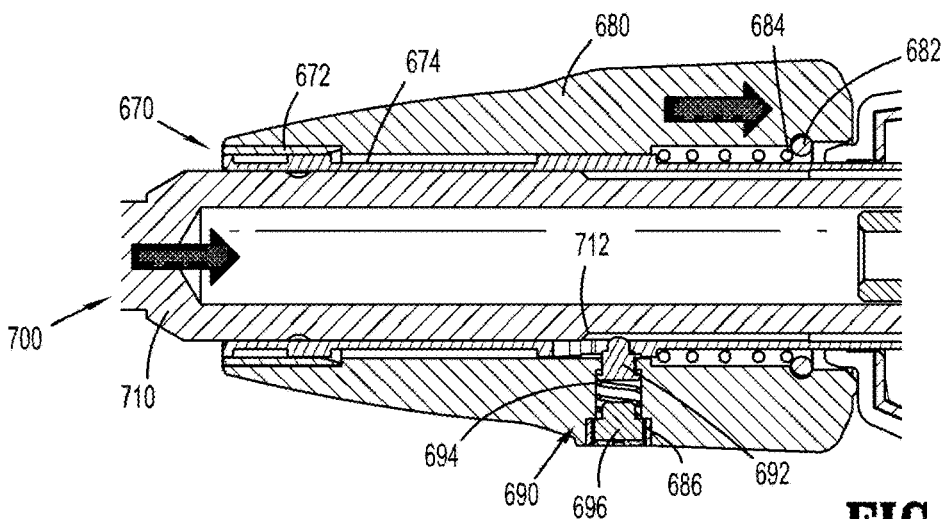
FIG. 12A is a side, longitudinal, cross-sectional view of the receiver assembly of the reusable handle assembly of FIG. 3, with the rotation knob disposed in a proximal position engaging the endoscopic assembly therein.
Figure 12B:
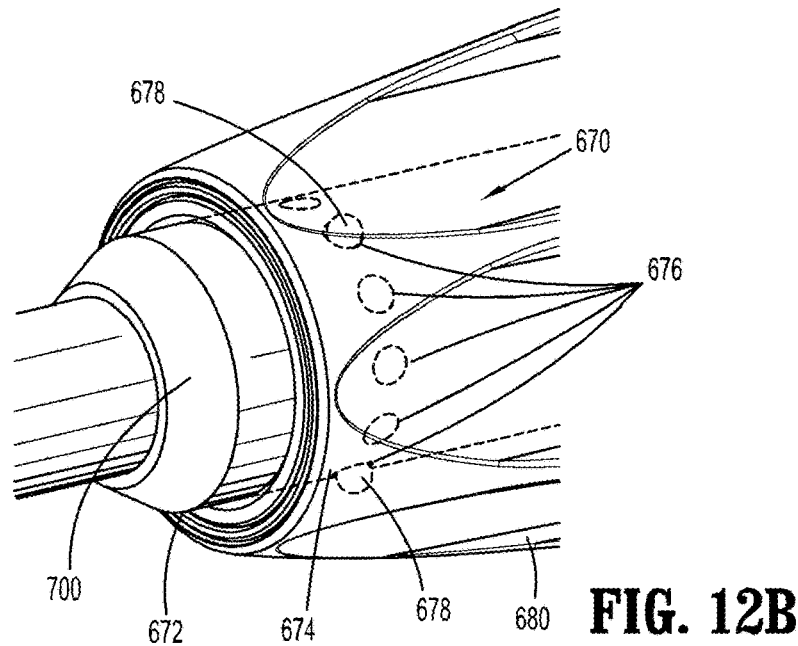
FIG. 12B is a side, perspective view of the indicated area in FIG. 12A, with the rotation knob shown transparent to illustrate the internal components therein.

Also referring to FIGS. 12A and 12B, with locking pin 692 disengaged from distal aperture 679b, rotation knob 680 is no longer locked relative to inner tubular member 674. Thus, once rotation knob 680 is unlocked from inner tubular member 674, biasing member 684 serves to bias rotation knob 680 proximally from the proximal position to the distal position, thereby moving outer collar 672 from the distal unlocked position to the proximal locked position. Upon movement of outer collar 672 to the proximal locked position, outer collar 672 urges ball bearings 678 inwardly such that the portions of ball bearings 678 extend through apertures 676 of inner tubular member 674 into the interior of inner tubular member 674 and into engagement within the corresponding apertures 714 of proximal hub 710 to thereby engage proximal hub 710 within receiver assembly 670. Further, with rotation knob 680 in the proximal locked position, locking pin 692 is aligned with proximal aperture 679a. As a result, biasing member 694 biases locking pin 692 into engagement with proximal aperture 679a to thereby lock rotation knob 680 and outer collar 672 relative to inner tubular member 674 and, consequently, lock proximal hub 710 in engagement within receiver assembly 670.

With proximal hub 710 of endoscopic clip-applying assembly 700 operably engaged within receiver assembly 670, as detailed above, handle assembly 500 (FIG. 1) may be actuated to form one or more surgical clips (not shown) of endoscopic clip-applying assembly 700 about tissue.

Figure 13:
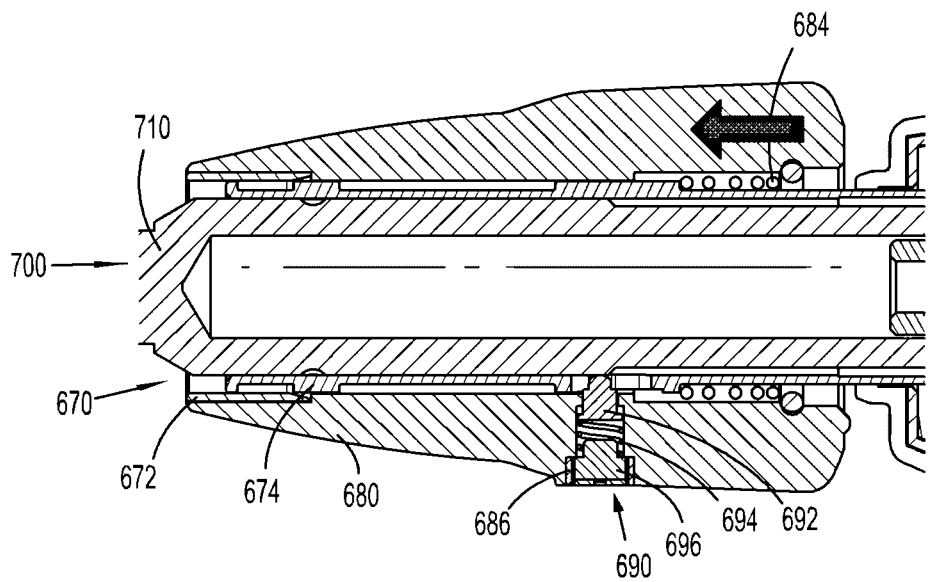
FIG. 13 is a side, longitudinal, cross-sectional view of the receiver assembly of the reusable handle assembly of FIG. 3, illustrating movement of the rotation knob from the proximal position to the distal position to disengage the endoscopic assembly therefrom.
Figure 14:
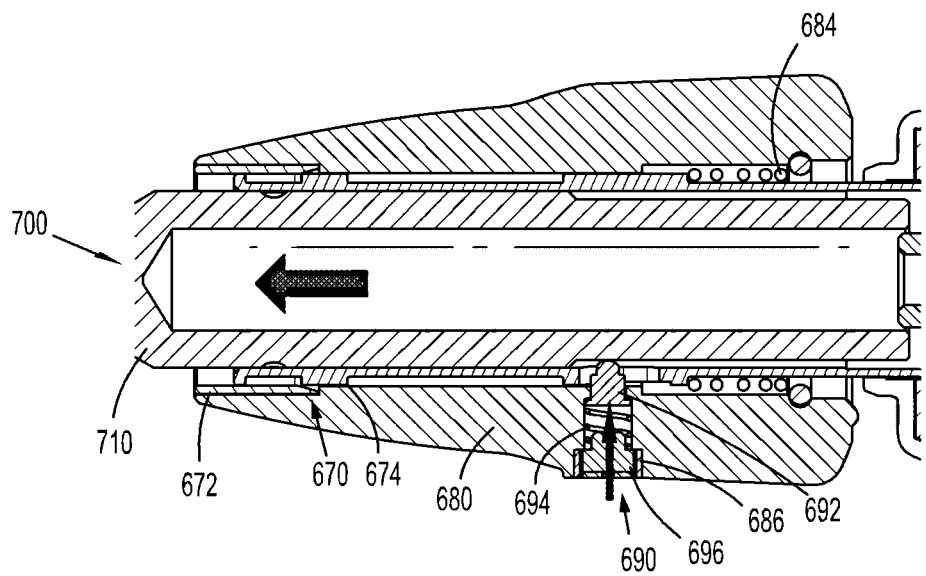
FIG. 14 is a side, longitudinal, cross-sectional view of the receiver assembly of the reusable handle assembly of FIG. 3, with the rotation knob disposed in the distal position after disengagement of the endoscopic assembly therefrom.

Turning now to FIGS. 13 and 14, at the completion of the surgical procedure, or when it is otherwise desired to remove endoscopic clip-applying assembly 700 from receiver assembly 670, the user grasps rotation knob 680 and translates rotation knob 680 distally from the proximal position towards the distal position with sufficient urging so as to dislodge locking pin 692 from proximal aperture 679a and enable movement of rotation knob 680 to the distal position. With rotation knob 680 in the distal position, outer collar 672 is disposed in the unlocked distal position. Thus, proximal hub 710 is disengaged from receiver assembly 670 and can be relatively easily removed from within inner tubular member 674, thereby fully disengaging endoscopic clip-applying assembly 700 from receiver assembly 670.

Figure 15:
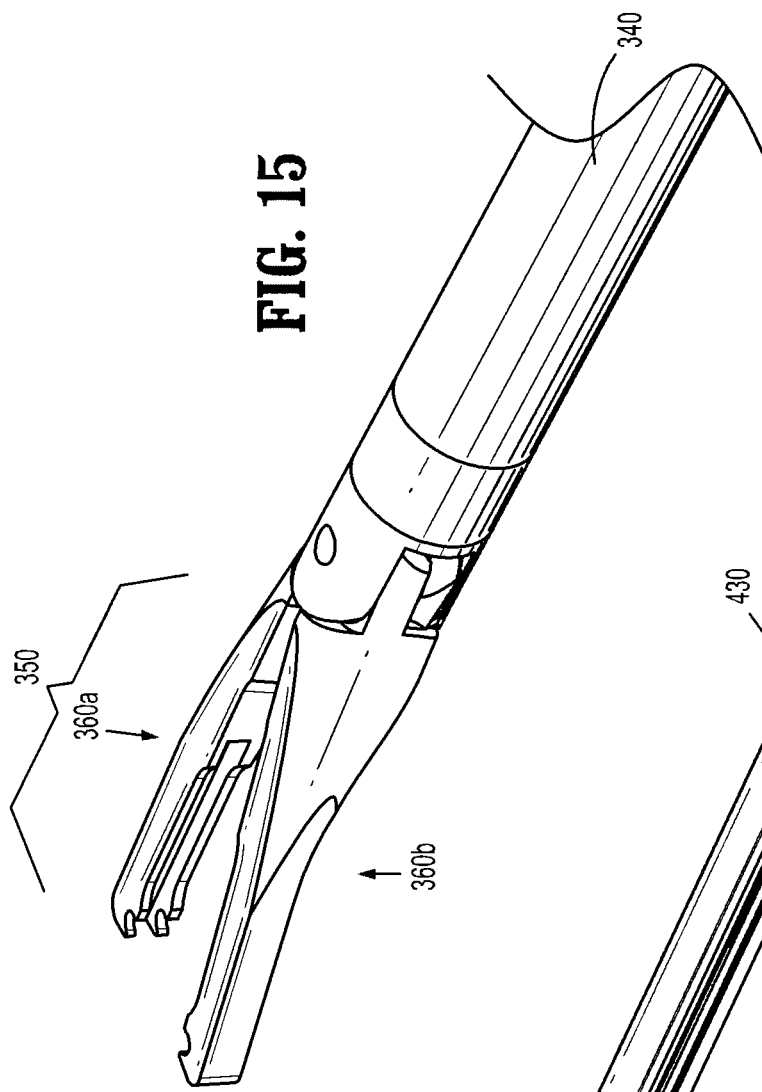
FIG. 15 is an enlarged, perspective view of the distal portion of an endoscopic assembly configured for use with the handle assembly of FIG. 1.

Referring to FIG. 15, an endoscopic assembly 300 provided in accordance with the present disclosure and configured for use with handle assembly 500 (FIG. 1) is shown. Endoscopic assembly 300 is configured for non-ratcheting use and, thus, when endoscopic assembly 300 is engaged with handle assembly 500, bypass assembly 550 is utilized to move ratchet pawl 542 to the bypass position (see FIG. 7), as detailed above.

Endoscopic assembly 300 generally includes a proximal hub (not shown), an inner drive assembly (not shown) disposed within and extending through the proximal hub, an elongated shaft 340 extending distally from the proximal hub, and an end effector assembly 350 including a pair of jaw members 360a, 360b disposed at the distal end of elongated shaft 340. Endoscopic assembly 300 is configured to grasp and/or manipulate tissue, retrieve a surgical clip, and to close, fire, or form the surgical clip about tissue. It is contemplated that endoscopic assembly 300 be configured to close, fire or form surgical clips similar to those shown and described in U.S. Pat. No. 4,834,096, the entire contents of which are incorporated herein by reference.

The proximal hub of endoscopic assembly 300 may include features similar to those of proximal hub 710 of endoscopic assembly 700 to enable releasable engagement of endoscopic assembly 300 with handle assembly 500 (FIG. 1), as detailed above. With additional reference to FIG. 3, when endoscopic assembly 300 is engaged with handle assembly 500 (FIG. 1), the inner drive assembly is operably positioned such that, upon advancement of drive bar 532 in response to actuation of trigger assembly 520, the drive bar 532 contacts and urges the inner drive assembly distally to thereby close jaw members 360a, 360b to fire a surgical clip loaded therebetween.

Figure 16:
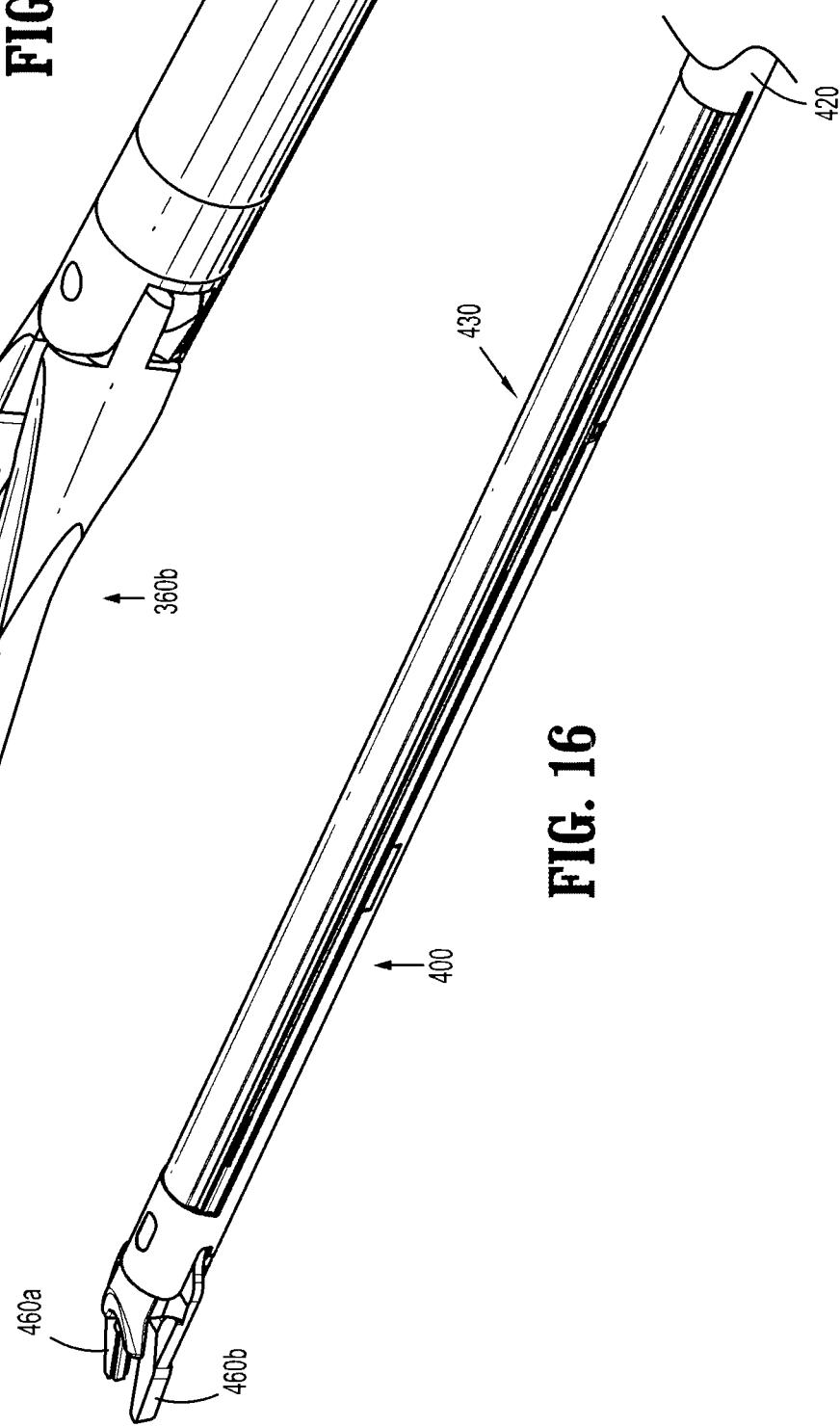
FIG. 16 is an enlarged, perspective view of the distal portion of another endoscopic configured for use with the handle assembly of FIG. 1.

Referring to FIG. 16, another endoscopic assembly 400 provided in accordance with the present disclosure and configured for use with handle assembly 500 (FIG. 1) is shown. Endoscopic assembly 400 is configured for ratcheting use and, thus, upon engagement of endoscopic assembly 400 with handle assembly 500, bypass assembly 550 is not manipulated such that ratchet pawl 542 remains in the use position, as detailed above, thus enabling engagement of ratchet pawl 540 with drive bar 532 to enable ratcheting use upon actuation of trigger assembly 520 (see FIG. 6).

Endoscopic assembly 400 generally includes a proximal hub (not shown), an inner drive assembly 430 disposed within and extending through the proximal hub, an elongated shaft 420 extending distally from the proximal hub, and a pair of jaw members 460a, 460b supported at the distal end of elongated shaft 420. Endoscopic assembly 400 is configured to close, fire, or form one or more surgical clips about tissue. More specifically, it is contemplated that endoscopic assembly 400 may be configured to close, fire or form surgical clips similar to those shown and described in U.S. Pat. No. 7,819,886 or 7,905,890, the entire contents of each of which is incorporated herein by reference.

The proximal hub of endoscopic assembly 400 may include features similar to those of proximal hub 710 of endoscopic assembly 700 to enable releasable engagement of endoscopic assembly 400 with handle assembly 500 (FIG. 1), as detailed above. With additional reference to FIG. 3, when endoscopic assembly 400 is engaged with handle assembly 500 (FIG. 1), inner drive assembly 430 is operably positioned such that, upon advancement of drive bar 532 in response to actuation of trigger assembly 520, the drive bar 532 contacts and urges the inner drive assembly 430 distally to thereby close jaw members 460a, 460b to fire a surgical clip loaded therebetween.

To the extent consistent, handle assembly 500 and/or endoscopic assemblies 400, 700 may include any or all of the features of the handle assembly and/or endoscopic assemblies disclosed and described in International Patent Application No. PCT/CN2015/080845, filed Jun. 5, 2015, entitled "Endoscopic Reposable Surgical Clip Applier," International Patent Application No. PCT/CN2015/091603, filed on Oct. 10, 2015, entitled "Endoscopic Surgical Clip Applier," and/or International Patent Application No. PCT/CN2015/093626, filed on Nov. 3, 2015, entitled "Endoscopic Surgical Clip Applier," the entire content of each of which being incorporated herein by reference.

Surgical instruments such as the clip appliers described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 17:
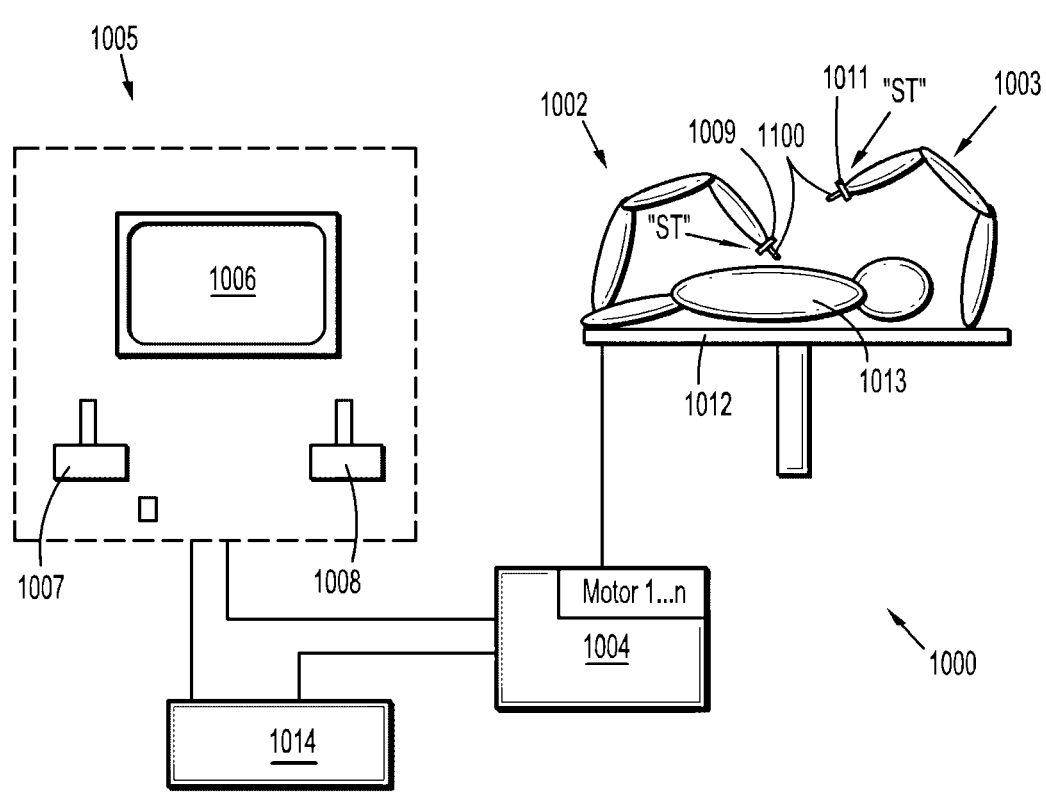
FIG. 17 is a schematic illustration of a robotic surgical system configured for use in accordance with the present disclosure.

Referring to FIG. 17, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Patent Publication No. 2012/0116416, filed on Nov. 3, 2011, entitled "Medical Workstation," the entire content of which is incorporated herein by reference, for a more detailed discussion of the construction and operation of an exemplary robotic surgical system.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
    a handle assembly including:
        a receiver assembly including an outer collar and an inner tubular member; and
        a rotation knob disposed about the receiver assembly, the rotation knob slidable relative to the inner tubular member and engaged to the outer collar such that sliding of the rotation knob relative to the inner tubular member between a proximal position and a distal position slides the outer collar relative to the inner tubular member between a proximal locked position and a distal unlocked position;
    an endoscopic clip-applying assembly insertable into the inner tubular member, wherein, with the endoscopic clip-applying assembly inserted into the inner tubular member, the rotation knob is slidable from the distal position to the proximal position to thereby slide the outer collar from the distal unlocked position to the proximal locked position to lock the endoscopic clip-applying assembly within the inner tubular member, wherein the receiver assembly is configured to releasably engage the endoscopic clip-applying assembly; and
    at least one ball bearing configured for insertion partially through a respective aperture defined within the inner tubular member, each ball bearing configured for receipt within a corresponding aperture defined within the endoscopic clip-applying assembly to lock the endoscopic clip-applying assembly within the inner tubular member.

2. The reposable surgical clip applier according to claim 1, wherein, in the proximal locked position of the outer collar, the outer collar urges the at least one ball bearing inwardly partially through the respective aperture of the inner tubular member and into engagement within the corresponding aperture defined within the endoscopic clip-applying assembly to lock the endoscopic clip-applying assembly within the inner tubular member.

3. A reposable surgical clip applier, comprising:
    a handle assembly including:
        a receiver assembly including an outer collar and an inner tubular member, wherein the inner tubular member defines a proximal aperture and a distal aperture; and
        a rotation knob disposed about the receiver assembly, wherein the rotation knob includes a locking pin operably coupled to the inner tubular member, the rotation knob slidable relative to the inner tubular member and engaged to the outer collar such that sliding of the rotation knob relative to the inner tubular member between a proximal position and a distal position slides the outer collar relative to the inner tubular member between a proximal locked position and a distal unlocked position, the locking pin being configured for engagement within the proximal aperture of the inner tubular member to lock the rotation knob in the proximal position and being configured for engagement within the distal aperture of the inner tubular member to lock the rotation knob in the distal position; and an endoscopic clip-applying assembly insertable into the inner tubular member, wherein, the receiver assembly is configured to releasably engage the endoscopic clip-applying assembly, wherein, with the endoscopic clip-applying assembly inserted into the inner tubular member, the rotation knob is slidable from the distal position to the proximal position to thereby slide the outer collar from the distal unlocked position to the proximal locked position to lock the endoscopic clip-applying assembly within the inner tubular member.

4. The reposable surgical clip applier according to claim 3, wherein, in the absence of the endoscopic clip-applying assembly, the rotation knob is locked in the distal position with the locking pin engaged within the distal aperture.

5. The reposable surgical clip applier according to claim 4, wherein insertion of the endoscopic clip-applying assembly into the inner tubular member disengages the locking pin from the distal aperture to permit movement of the rotation knob to the proximal position.

6. The reposable surgical clip applier according to claim 5, further including a biasing member configured to bias the rotation knob towards the proximal position such that, upon disengagement of the locking pin from the distal aperture, the rotation knob is urged to the proximal position under the bias of the biasing member.

7. The reposable surgical clip applier according to claim 3, further including at least one ball bearing configured for insertion partially through a respective aperture defined within the inner tubular member, each ball bearing configured for receipt within a corresponding aperture defined within the endoscopic clip-applying assembly to lock the endoscopic clip-applying assembly within the inner tubular member.

8. The reposable surgical clip applier according to claim 7, wherein, in the proximal locked position of the outer collar, the outer collar urges the at least one ball bearing inwardly partially through the respective aperture of the inner tubular member and into engagement within the corresponding aperture defined within the endoscopic clip-applying assembly to lock the endoscopic clip-applying assembly within the inner tubular member.

\* \* \* \* \*